(12) United States Patent
Rennie et al.

(10) Patent No.: US 11,701,382 B2
(45) Date of Patent: Jul. 18, 2023

(54) TREATMENT OF POST-OPERATIVE JOINT PAIN WITH POLYSULFATED POLYSACCHARIDES

(71) Applicant: PARADIGM BIOPHARMACEUTICALS LTD., Melbourne (AU)

(72) Inventors: Paul Rennie, West Beach (AU); Ravi Krishnan, Royston Park (AU)

(73) Assignee: PARADIGM BIOPHARMACEUTICALS LTD, Melbourne (AU)

( * ) Notice: Subject to any disclaimer, the term of this patent is extended or adjusted under 35 U.S.C. 154(b) by 0 days.

(21) Appl. No.: 16/976,671

(22) PCT Filed: Feb. 27, 2019

(86) PCT No.: PCT/AU2019/050163
§ 371 (c)(1),
(2) Date: Aug. 28, 2020

(87) PCT Pub. No.: WO2019/165498
PCT Pub. Date: Sep. 6, 2019

(65) Prior Publication Data
US 2021/0000862 A1    Jan. 7, 2021

(30) Foreign Application Priority Data

Feb. 28, 2018  (AU) .............................. 2018900650

(51) Int. Cl.
*A61K 31/737* (2006.01)
*A61K 9/00* (2006.01)

(52) U.S. Cl.
CPC .......... *A61K 31/737* (2013.01); *A61K 9/0019* (2013.01)

(58) Field of Classification Search
CPC ........................ A61K 31/737; A61P 19/00–10
See application file for complete search history.

(56) References Cited

U.S. PATENT DOCUMENTS

| 2002/0068718 A1 | 6/2002 | Pierce |
| 2016/0038531 A1 | 2/2016 | Sullivan et al. |

FOREIGN PATENT DOCUMENTS

| WO | 0241901 A1 | 5/2002 |
| WO | 2008144836 A1 | 12/2008 |
| WO | 2012103588 A1 | 8/2012 |
| WO | 2019023761 A1 | 2/2019 |

OTHER PUBLICATIONS

Jacobs, C. et al "Subchondral bone marrow edema . . . " J. Arthroplasty, vol. 31, pp. 491-494. (Year: 2016).*
Gandhi, R. et al "Inflammatory predictors of ongoing pain . . . " The Knee, vol. 20, pp. 316-318. (Year: 2013).*
Bonnin M., "Failure mechanisms in total knee arthroplasty" In: Osteoarthritis of the knee. Springer, Paris. https://doi.org/10.1007/978-2-287-74175-3_13. (Year: 2008).*
Pollice, P. et al "Oral pentoxifylline inhibits release of tumor necrosis factor-alpha . . . " J. Bone Joint Surg., vol. 83, No. 7, pp. 1057-1061. (Year: 2001).*
Elmesiry, A. et al "Pentosan polysulfate as a disease modifier . . . " J. Arthritis, vol. 5, iss 3, pp. 1-10. (Year: 2016).*
Ghosh, P. et al "Effects of pentosan polysulfate in osteoarthritis . . . " Curr. Ther. Res., vol. 66, No. 6, pp. 552-571. (Year: 2005).*
Gupta, S. et al "Review article: osteolysis after total knee arthroplasty" J. Arthroplasty, vol. 22, No. 6, 787-799. (Year: 2007).*
Altahawi, F.F. et al., "Comparing an accelerated 3D fast spin-echo sequence (CS-SPACE) for knee 3-T magnetic resonance imaging with traditional 3D fast spin-echo (SPACE) and routine 2D sequences", Skeletal radiology; 46(1), 2016, 7-15.
Anderson, V.R. et al., "Pentosan polysulfate: a review of its use in the relief of bladder pain or discomfort in interstitial cystitis", Drugs; 66(6), 2006, 821-835.
Batemen, D. et al., "Non-steroidal anti-inflammatory drugs and elderly patients", British Medical Journal; 310, 1995, 817-818.
Brandt, K.D., "Should nonsteroidal anti-inflammatory drugs be used to treat osteoarthritis?", Rheumatic Disease Clinics of North America; 19, 1993, 29-44.
Briggs, K.K. et al., "Reliability, validity, and responsiveness of the Lysholm knee score and Tegner activity scale for patients with meniscal injury of the knee", The Journal of bone and joint surgery American vol. 88(4), 2006, 698-705.
Davies-Tuck, M.L., "The natural history of bone marrow lesions in community-based adults with no clinical knee osteoarthritis", Annals of the Rheumatic Diseases.; 68(6), 2009, 904-908.
Davis, E.L. et al., "Safety and efficacy of the use of intravesical and oral pentosan polysulfate sodium for interstitial cystitis: a randomized double-blind clinical trial", J Urol; 179(1), 2008, 177-185.

(Continued)

*Primary Examiner* — Leigh C Maier
(74) *Attorney, Agent, or Firm* — Dorsey & Whitney LLP

(57) ABSTRACT

The present invention relates to medical use of polysulfated polysaccharides and compositions thereof in the treatment of post-operative joint pain in a mammal. In particular, the invention relates to the use of the polysulfated polysaccharide, pentosan polysulfate, and compositions thereof in the treatment of aseptic persistent pain after joint arthroplasty in a mammal.

23 Claims, No Drawings

(56) References Cited

OTHER PUBLICATIONS

Dimitrakov, J. et al., "Pharmacologic management of painful bladder syndrome/interstitial cystitis: a systematic review", Arch Intern Med; 167(18), 2007, 1922-1929.
Felson, D.T., "Bone marrow edema and its relation to progression of knee osteoarthritis", Annals of internal medicine; 139(5 Pt 1), 2003, 330-336.
Felson, D.T. et al., "The association of bone marrow lesions with pain in knee osteoarthritis", Annals of internal medicine;134(7), 2001, 541-549.
Guo, D. et al., "Continuous intra-articular infusion anesthesia for pain control after total knee arthroplasty: study protocol for a randomized controlled trial", Trials; 15:245, 2014.
Hjermstad, M.J. et al., "Studies comparing Numerical Rating Scales, Verbal Rating Scales, and Visual Analogue Scales for assessment of pain intensity in adults: a systematic literature review", Journal of pain and symptom management; 41(6), 2011, 1073-1093.
Hunter, D.J. et al., "Increase in bone marrow lesions associated with cartilage loss: a longitudinal magnetic resonance imaging study of knee osteoarthritis", Arthritis and rheumatism; 54(5), 2006, 1529-1535.
Krupinski, K. et al., "Anticoagulant and antithrombotic effects of chemically modified heparins and pentosan polysulfate", Haemostasis; 20(2), 1990, 81-92.
Laslett, L.L. et al., "Zoledronic acid reduces knee pain and bone marrow lesions over 1 year: a randomised controlled trial", Ann Rheum Dis.; 71(8), 2012, 1322-1328.
Lim, H.A. et al., "Causes of Aseptic Persistent Pain after Total Knee Arthroplasty", Clinics in Orthopedic Surgery; 2017;9(1):50-56., 2017, 50-56.
Losonczy, H., "Effect of pentosan polysulfate on activated partial thromboplastin time, thrombin time, euglobulin clot lysis and tissue-type plasminogen activator and plasminogen activator inhibitor activities in patients with thromboembolic disease", Semin Thromb Hemost; 17(4), 1991, 394-398.
Lowitz, T., "Bone marrow lesions identified by MRI in knee osteoarthritis are associated with locally increased bone mineral density measured by QCT", Osteoarthritis and cartilage.; 21(7), 2013, 957-964.
Mayerhoefer, M.E. et al., "Short-term outcome of painful bone marrow oedema of the knee following oral treatment with iloprost or tramadol: results of an exploratory phase II study of 41 patients", Rheumatology; 46(9), 2007, 1460-1465.
Miyata, N. et al., "Pentosan reduces osteonecrosis of femoral head in SHRSP", Clinical and experimental hypertension (New York, NY : 1993); 32(8), 2010, 511-516.
O'Mahony, D., "Prevention of corticosteroid-induced osteoporosis and fractures", Journal of Clinical Pharmacy and Therapeutics; 24(2), 1999, 83-85.
Raynauld, J.P. et al., "Correlation between bone lesion changes and cartilage volume loss in patients with osteoarthritis of the knee as assessed by quantitative magnetic resonance imaging over a 24-month period", Ann Rheum Dis.;67(5), 2008, 683-688.
Roemer, F.W., "Change in MRI-detected subchondral bone marrow lesions is associated with cartilage loss: the MOST Study. A longitudinal multicentre study of knee osteoarthritis", Ann Rheum Dis.; 68(9), 2009, 1461-1465.
Roos, E.M. et al., "Knee injury and Osteoarthritis Outcome Score (KOOS): from joint injury to osteoarthritis", Health Qual Life Outcomes; 1:64, 2003.
Scully, M.F. et al., "Anticoagulant and antiheparin activities of a pentosan polysulphate", Thrombosis Research; 31(1), 1983, 89-97.
Shanmugam, M. et al., "Heparinoid-active sulphated polysaccharides from marine algae as potential blood anticoagulant agents", Current Science; 79(12), 2000, 1672-1683.
Starr, A.M. et al., "Bone marrow edema: pathophysiology, differential diagnosis, and imaging", Acta radiologica (Stockholm, Sweden: 1987); 49(7), 2008, 771-786.
Tanamas, S.K., "Bone marrow lesions in people with knee osteoarthritis predict progression of disease and joint replacement: a longitudinal study", Rheumatology (Oxford, England); 49(12), 2010, 2413-2419.
Varenna, M. et al., "Intravenous neridronate in the treatment of acute painful knee osteoarthritis: a randomized controlled study", Rheumatology (Oxford, England).; 54(10), 2015, 1826-1832.
Vinazzer, H., "Prevention of recurrence of cerebrovascular thromboses. A randomized comparative study acetylsalicylic acid and sodium pentosan polysulfate", Fortschr Med; 105(5), 1987, 79-85.
Vongchan, P. et al., "Anticoagulant activities of the chitosan polysulfate synthesized from marine crab shell by semi-heterogeneous conditions", Science Asia; 29, 2003, 115-120.
Wikipedia,, "Pentosan Polysulfate", https://en.wikipedia.org/w/index.php?title=Pentosan_polysulfate&oldid=819309952, Jun. 25, 2019, 6 pages.
Wluka, A.E. et al., "Bone marrow lesions predict increase in knee cartilage defects and loss of cartilage volume in middle-aged women without knee pain over 2 years", Ann Rheum Dis; 68, 2009, 850-855.
Wluka, A.E. et al., "Bone marrow lesions predict progression of cartilage defects and loss of cartilage volume in healthy middle-aged adults without knee pain over 2 yrs", Rheumatology (Oxford, England);47(9), 2008, 1392-1396.
Xu, X. et al., "Efficacy of intra-articular magnesium for postoperative analgesia in total hip arthroplasty", Biomedical Reports; 6, 2017, 232-236.
Zhai, G. et al., "Correlates of knee pain in older adults: Tasmanian Older Adult Cohort Study", Arthritis and rheumatism; 55(2), 2006, 264-271.
Extended European Search Report for European Patent Application No. 19759993.9 dated Oct. 25, 2021, 8 pages.
Kumagai, Kenji et al., "Sodium pentosan polysulfate resulted in cartilage improvement in knee osteoarthritis—An open clinical trial—11", BMC Clinical Pharmacology, Biomed Central, London, GB, vol. 10, No. 1, Mar. 28, 2010 (Mar. 28, 2010) , p. 7.
Sampson, et al., "Improved clinical outcome measures of knee pain and function with concurrent resolution of subchondral Bone Marrow Edema Lesion and joint effusion in an osteoarthritic patient following Pentosan Polysulphate Sodium treatment: a case report", BMC Musculoskeletal Disorders, vol. 18, No. 1, Sep. 12, 2017 (Sep. 12, 2017), pp. 1-5.
Kuttapitiya, et al., "Microarray analysis of bone marrow lesions in osteoarthritis demonstrates upregulation of genes implicated in osteochondral turnover, neurogenesis and inflammation", Ann. Rheum. Dis., Oct. 2017;76(10):1764-1773, 10 pages.
Bonnin, M. et al., "Osteoarthritis of the Knee", Springer-Verlag, France, 2008, 635 pages.

* cited by examiner

TREATMENT OF POST-OPERATIVE JOINT PAIN WITH POLYSULFATED POLYSACCHARIDES

CROSS-REFERENCE TO RELATED APPLICATIONS

This application is a national stage application under 35 U.S.C. § 371 of International Application No. PCT/AU2019/050163 filed Feb. 27, 2019, entitled "TREATMENT OF POST-OPERATIVE JOINT PAIN WITH POLYSULFATED POLYSACCHARIDES" which claims priority to Australian Patent Application No. 2018900650 filed Feb. 28, 2018, the contents of each of which is hereby incorporated herein in their entirety by reference.

TECHNICAL FIELD

This invention relates to the medical use of polysulfated polysaccharides and compositions thereof for the treatment of post-operative joint pain in a mammal. In particular, the invention relates to the use of polysulfated polysaccharides in the treatment of aseptic persistent pain after joint arthroplasty.

BACKGROUND

Post-Operative Pain in Joint Arthroplasty

Joint arthroplasty or replacement provides an opportunity for a patient to live free from the pain of debilitating diseases such as end-stage osteoarthritis and rheumatoid arthritis where non-surgical treatment has proved to be unsuccessful. Nonetheless, although joint arthroplasty offers good pain relief and improves quality of life, up to 20% of patients complain of persistent pain [1]. In particular, aseptic persistent pain may not be resolved even one year after surgery. This is clearly dissatisfying to the patient who has opted for joint arthroplasty to reduce pain. Further, unsatisfactory clinical outcomes increase the cost to the healthcare system.

Early and accurate diagnosis of post-operative joint pain is key to optimising treatment. Whereas the diagnosis of septic pain or pain caused by periprosthetic fracture is relatively obvious the diagnosis of aseptic pain is not so clear. Thus, the successful treatment of aseptic persistent post-operative joint pain is made difficult.

A recent study shows that aseptic persistent joint pain following total knee arthroplasty may result from extra-articular causes, such as extra-articular osteoarthritis or avascular necrosis, or, in the majority, a number of intra-articular causes including prosthetic loosening, prosthetic wear, instability, recurrent hemarthrosis, patellar maltracking, tendon rupture and stiffness. Treatment of the aseptic persistent pain is reported to ultimately involve revision surgery [1].

Revision surgery is complicated, comes with the risk that pain will not diminish, and in some cases can be detrimental. The alternative is standard non-surgical treatment involving the use of analgesic or anti-inflammatory medications combined with reduced weight-bearing and physical therapy [2]. However, non-steroidal anti-inflammatory drugs (NSAIDs) and corticosteroids have been found to have negative effects on bone healing and the metabolism of cartilage ([3]-[6]). The risk of fracture, both traumatic and spontaneous, is increased in those subjects that take continuous corticosteroid therapy [5].

Thus, there is a need for pharmaceuticals that do not have the negative effects of NSAIDs or corticosteroids to expand the limited number of options currently available for managing post-operative joint pain, in particular, aseptic persistent pain which is difficult to diagnose and difficult to treat.

Polysulfated Polysaccharides

Heparin and structurally related polysulfated polysaccharides such as pentosan polysulfate, chitosan polysulfate, the fucans etc have been used for a number of years as anticoagulants [7-12]. Pentosan polysulfate (PPS) is a weaker anticoagulant than heparin [7, 9, 11] but has been used post-surgically and prophylactically as a thrombolytic agent [12]. When given via the oral and intrathecal routes, PPS has been used for the treatment of interstitial cystitis (inflammation of the bladder) [13-15]. Indeed, PPS is the active agent in the drug ELMIRON® which is currently prescribed for interstitial cystitis. The potential use of PPS in treatment of inflammatory conditions such as asthma, allergic rhinitis, and/or chronic obstructive pulmonary disease (COPD) has also been described [16], as has the use of PPS in osteoporosis [17]; and the use of PPS in bone marrow edema [18].

SUMMARY

The present invention is based on the surprising finding that PPS treatment reduces persistent, post-operative pain in a subject following joint arthroplasty. The present invention is also based on the surprising finding that PPS treatment reduces osteoarthritic pain and persistent, post-operative joint pain in a subject. Further to the reduction of pain, PPS treatment is found to improve joint function and to reduce bone marrow edema lesions with no adverse events reported.

Therefore, PPS may be an improved alternative pharmaceutical option to NSAIDs and corticosteroids with potential pain reducing activity. The findings implicate the potential effectiveness of PPS as a treatment option in subjects suffering from post-operative pain and as a treatment option in subjects suffering from post-operative pain and from arthritic conditions such as osteoarthritis.

According to a first aspect, there is provided a method for the treatment of post-operative joint pain in a mammal, the method comprising the step of administering a polysulfated polysaccharide or an acceptable salt thereof, to the mammal.

According to a second aspect, there is provided a composition comprising a polysulfated polysaccharide or an acceptable salt thereof, and an acceptable excipient for the treatment of post-operative joint pain in a mammal.

According to a third aspect, there is provided a composition comprising a polysulfated polysaccharide or an acceptable salt thereof, and an acceptable excipient for use in the treatment of post-operative joint pain in a mammal.

According to a fourth aspect, there is provided use of a polysulfated polysaccharide or an acceptable salt thereof, in the treatment of post-operative joint pain in a mammal.

According to a fifth aspect, there is provided use of a polysulfated polysaccharide or an acceptable salt thereof, in the manufacture of a medicament for the treatment of post-operative joint pain in a mammal.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. Thus, the term "an articulating joint" means "one or more articulating joints" unless the context clearly indicates otherwise.

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 2, from 1 to 3, from 1 to 4, from 2 to 3, from 2 to 4, from 2 to 5, from 3 to 4 etc., as well as individual and partial numbers within the recited range, for example, 1, 2, 3, 4, and 5. This applies regardless of the breadth of the disclosed range. Where specific values are required, these will be indicated in the specification.

The term "acceptable excipient" includes excipients or agents such as solvents, diluents, dispersion media, coatings, antibacterial and antifungal agents, isotonic and absorption delaying agents and the like that are physiologically compatible and are not deleterious to a compound as described herein or use thereof. The use of such carriers and agents to prepare compositions of pharmaceutically active substances is well known in the art (see, for example *Remington: The Science and Practice of Pharmacy*, 21st Edition; Lippincott Williams & Wilkins: Philadelphia, Pa., 2005).

The term "acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of acceptable salts and their formation is known to those skilled in the art and is as described in general texts such as "*Handbook of Pharmaceutical salts*" P. H. Stahl, C. G. Wermuth, 1$^{st}$ edition, 2002, Wiley-VCH.

The terms "administration of" and or "administering a" compound should be understood to mean providing a compound of the invention to the individual in need of treatment.

The term "composition" as used herein is intended to encompass a product comprising the specified ingredients in the specified amounts, as well as any product which results, directly or indirectly, from combination of the specified ingredients in the specified amounts.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

This invention is directed to treatments of mammal subjects. The treatment of a "mammal" subject may also be referred to the treatment of a "patient" or an "individual". A "mammal" subject has presented a clinical manifestation of a particular symptom or symptoms suggesting the need for treatment, is treated for a condition, or who has been diagnosed with a condition to be treated.

Thus, the invention is to be understood to be applicable to humans and other non-human mammals unless specifically indicated otherwise. The human can be male or female. Other non-human mammals may be a primate, livestock and farm animals (e.g. sheep, horses, cattle, pigs), domestic pets, such as cats and dogs, performance animal (e.g. racehorses, camels, greyhounds), laboratory test animals (e.g. mice, rabbits, rats, guinea pigs) as well as those mammals that usually exist in the wild but may be susceptible to treatment by virtue of such mammals being situated in zoos, wildlife parks and the like.

As used herein, the terms "treating", "treat" or "treatment" and variations thereof, refer to clinical intervention designed to alter the natural course of the subject during the course of clinical pathology. Desirable effects of treatment include decreasing the rate of disease progression, ameliorating or palliating the disease state, and remission or improved prognosis. A subject is successfully "treated", for example, if one or more of the above treatment outcomes is achieved. As used herein, the terms "treating", "treat" or "treatment" and variations thereof encompass "preventing", "prevent" or "prevention" which would be understood to refer to clinical intervention designed to avert the development of a course of clinical pathology.

An "effective amount" encompasses a "therapeutically effective" amount which refers to at least the minimum concentration or amount required to effect a measurable improvement of a particular disease (e.g., bone marrow edema). An effective amount herein may vary according to factors such as the disease state, age, sex, and weight of the patient, and the ability of the PPS to elicit a desired response in the individual. An effective amount is also one in which any toxic or detrimental effects of the PPS are outweighed by the therapeutically beneficial effects. An "effective amount" also encompasses a "prophylactically effective" amount which refers to the amount of drug or the rate of drug administration needed to produce the desired preventive result.

DESCRIPTION OF EMBODIMENTS

The present disclosure relates to a method for the treatment of post-operative joint pain in a mammal, the method comprising the step of administering a polysulfated polysaccharide or an acceptable salt thereof, to the mammal.

Preferably, the post-operative joint pain is in at least one articulating joint. The at least one articulating joint is preferably selected from the group consisting of: an ankle, elbow, a finger, hip, knee, shoulder, and wrist. Preferably, the at least one articulating joint is a knee.

Preferably, the post-operative pain results from a joint arthroplasty.

The joint arthroplasty is preferably a total joint arthroplasty. Preferably, the total joint arthroplasty is selected from the group consisting of: a total ankle arthroplasty, a total elbow arthroplasty, a total finger arthroplasty, a total hip arthroplasty, a total knee arthroplasty, a total shoulder arthroplasty, and a total wrist arthroplasty. The total joint arthroplasty is preferably a total knee arthroplasty.

The joint arthroplasty is preferably a partial joint arthroplasty. Preferably, the partial joint arthroplasty is selected from the group consisting of: a partial ankle arthroplasty, a partial elbow arthroplasty, a partial finger arthroplasty, a partial hip arthroplasty, a partial knee arthroplasty, a partial shoulder arthroplasty, and a partial wrist arthroplasty. The partial joint arthroplasty is preferably a partial knee arthroplasty.

Preferably, the post-operative joint pain is selected from the group consisting of: acute pain; chronic pain; general pain and persistent pain. The post-operative joint pain is preferably persistent pain. Preferably, the persistent pain is septic persistent pain. The persistent pain is preferably caused by periprosthetic fracture.

Preferably, the persistent pain is aseptic persistent pain. The aseptic persistent pain is preferably intra-articular aseptic persistent pain. Preferably, the intra-articular aseptic persistent pain is caused by a condition selected from the group comprising: aseptic prosthetic loosening, prosthetic wear, instability, recurrent hemarthrosis, patellar maltracking, tendon rupture and stiffness. The aseptic persistent pain is preferably extra-articular aseptic persistent pain. Preferably, the extra-articular aseptic persistent pain is caused by an extra-articular osteoarthritis or extra-articular avascular necrosis.

Preferably, the mammal is suffering from an additional arthritic condition further to the post-operative joint pain. The additional arthritic condition is preferably selected from rheumatoid arthritis or osteoarthritis. Preferably, the additional arthritic condition is rheumatoid arthritis. The additional arthritic condition is preferably osteoarthritis. Preferably, the osteoarthritis is degenerative osteoarthritis. The additional arthritic condition is preferably in a second joint different from the joint affected by the post-operative pain. Preferably, the second joint is one knee joint and the joint affected by the post-operative pain is another knee joint. The second knee joint is preferably the left knee joint and the joint affected by the post-operative pain is the right knee joint in a human patient.

Preferably, the polysulfated polysaccharide is selected from the group consisting of: high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

Preferably, the polysulfated polysaccharide is selected from the group consisting of: high molecular weight heparin, low molecular weight heparins, the heparan sulfates, pentosan polysulfate (PPS), chondroitin polysulfate and chitosan polysulfate. Preferably, the polysulfated polysaccharide is selected from the group consisting of: high molecular weight heparin, low molecular weight heparins, pentosan polysulfate (PPS), chondroitin polysulfate and chitosan polysulfate.

Preferably, the pentosan polysulfate (PPS) is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

Preferably, the pentosan polysulfate (PPS) is sodium pentosan polysulfate (NaPPS).

In one preferred embodiment, NaPPS is manufactured to the specifications lodged with the US FDA and European Community EMEA by Bene-PharmaChem GmbH & Co KG, Geretsried, Germany.

Preferably, the treatment is by administering the polysulfated polysaccharide or the acceptable salt thereof to the mammal in an effective amount of about 0.5 to about 2 mg/kg of the mammal per dose. The effective amount is preferably in the range of about 0.5 to about 1 mg/kg; about 1.0 to about 1.5 mg/kg or about 1.5 to about 2.0 mg/kg of the mammal per dose. Preferably, the effective amount is about 0.5 mg/kg, 1.0 mg/kg or 2.0 mg/kg of the mammal per dose. The effective amount is preferably about 2 mg/kg of the mammal per dose.

Preferably, the treatment is by administering the polysulfated polysaccharide or the acceptable salt thereof to the mammal in an effective amount, wherein the effective amount is a fixed dose in the range of about 25 mg to about 4000 mg. The fixed dose is preferably about 25 mg, about 50 mg, about 75 mg, about 100 mg, about 125 mg, about 150 mg, about 175 mg, about 200 mg, about 225 mg, about 250 mg, about 275 mg or about 300 mg. Preferably, the fixed dose is about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 2000 mg, about 3000 mg or about 4000 mg.

It will be recognized by persons skilled in the art, that PPS and PPS compositions suitable for administration by a variety of routes may be formulated by reference to standard textbooks in this field, such as *Remington: The Science and Practice of Pharmacy,* 21st Edition; Lippincott Williams & Wilkins: Philadelphia, Pa., 2005). These compositions include by injection, oral (including tablets and capsules containing gastro-intestinal drug absorption extenders and enhancers), intravenous and the like.

Preferably, the treatment is: by administering an injection; by topical administration; via suppositories or by oral administration. The treatment is preferably by administering an injection. Preferably, the injection is selected from a subcutaneous (SC) injection, an intramuscular (IM) injection, intravenous (IV) injection, intra-articular (IA) injection or a peri-articular injection. The treatment is preferably by administering a subcutaneous (SC) injection. Preferably, the subcutaneous (SC) injection is a slow SC injection.

Preferably, administration to a human is by dosing in a treatment regimen once daily, twice weekly or thrice weekly. Administration to a human is preferably by dosing in a treatment regimen twice weekly. Preferably, administration to a human is by dosing in a treatment regimen twice weekly with a minimum of three days and a maximum of four days between dosages. Administration to a human is preferably by dosing in a treatment regimen twice weekly for three weeks. Preferably, administration to a human is by dosing in a treatment regimen twice weekly for six weeks.

Preferably, the total dose of polysulfated polysaccharide administered in the treatment regimen is about 200 to 4000 mg.

It would be recognised that the treatment may be adapted to the individual. For example, the dosage would be adjusted accordingly for heavier or lighter weighted individuals. The treatment regimen may also be adapted according to the severity of the pain experienced by the subject. In some instances where a patient is experiencing high level pain, it is desirable to reach a therapeutic loading of the PPS as quickly as possible. This may necessitate, for example, the administration of about 1.0 mg/kg or more PPS daily until the pain is resolved.

When administration is by injection, this would normally be carried out in a clinical situation by a nurse/doctor. The person skilled in the art would understand that the key to successful treatment is to administer sufficient PPS to the subject to achieve an optimum therapeutic dose in the vicinity of the tissue lesion. Since it is known that PPS accumulates in connective tissues, loading can be achieved over time, eg daily doses of 1 mg PPS/kg over 4-5 days. It would be expected that for severe chronic cases the subject may require more than one course of treatment per year maybe twice or thrice per year.

From a safety point of view a lower dose range (1-2 mg PPS/kg or a fixed dose of about 25-50 mg) over a longer period and with decreased frequency of administration is preferred. This is because PPS is a known anticoagulant and the basal APT may be elevated with the higher dose (>3 mg PPS/kg or a fixed dose of about 150-200 mg) which could potentially encourage bleeding of any open wounds.

Whilst administration by injection is preferred, oral or topical formulations of PPS may be used as follow-up (maintenance dose) for the initial IM or SC PPS treatments. This would also be applicable to oral dosing. For administration by IV infusion, the lower doses of 0.5-1 mg PPS/kg daily are preferred.

The present disclosure also contemplates co-administration of other therapeutic agents with polysulfated polysaccharides. When other therapeutic agents are employed in combination with the compounds of the present invention they may be used for example in amounts as noted in the Physician Desk Reference (PDR) or as otherwise determined by one of ordinary skill in the art.

It will be understood, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. For example, it would be understood that large animals require larger doses. For illustration, a large animal like a horse may require a fixed dose of about 4000 mg.

The determination of the suitability of the treatment of the present disclosure may be established through the use of an imaging technique. For example, the diagnosis of joint conditions, disease or disorders may be performed by the diagnosis of bone marrow edema lesions (BMELs) through the use of MRI.

Bone Marrow Edema Lesions

Bone marrow edema lesions (BMEL) are changes that occur in the subchondral bone and are detected by MRI depicting the severity of symptoms including pain ([19]-[21]) and cartilage degeneration ([22]-[25]) in, for example, osteoarthritic patients. BMELs are generally evaluated using fat-suppressed proton density or T2-weighted sequences. In fat suppressed T2-weighted and fat suppressed proton density weighted sequences BMELs appear as hyper-intense signals [26].

The MRI signals related to the BMELs are thought to arise from an increase in concentration of blood and interstitial fluids (including infiltrating macrophages) in areas of trabecular microfractures and collapse within the bone marrow [26]. Improved spatial resolution and multiplanar reconstructions provide a potential role of 3D fast spin echo sequences, particularly for imaging of cartilage [27].

In this regard, the assessment of BMELs using MRI has gained considerable interest in monitoring osteoarthritic conditions such as knee osteoarthritis.

BMELS and Knee Osteoarthritis

Patients with knee osteoarthritis may exhibit BMELs that appear as areas of increased signal intensity on MRI of the knee, and in established disease BMELs are associated with knee pain [20], disease severity and disease progression including radiological progression of knee osteoarthritis [28] and cartilage loss based on MRI ([23], [29]). Furthermore, in progressive osteoarthritis BMELs are more likely to persist and enlarge in size with an associated increase in cartilage loss [23]. Moreover, the severity of BMEL has been shown to correlate with the risk of knee arthroplasty [30].

The strong association with BMEL with pain and loss of cartilage has heightened pharmaceutical interest to target this structural lesion for monitoring joint disease progression and therapy in, for example, knee osteoarthritis ([31]-[33]). Thus, not only has the imaging of BMELS by MRI become a tool for the diagnosis of conditions, diseases or disorders that affect joints, but a tool for the measurement of clinical outcomes.

The present disclosure contemplates reduction of pain in a mammal and/or improvement of function in a mammal as a clinical outcome. Clinical outcomes may also be measured using patient reported outcome measurement instruments. Patient reported pain and/or functional outcomes may be used. These include the Numerical Rating Scale (NRS) for pain [34]; the Lysholm Knee Score for function [35]; Knee injury and Osteoarthritis Outcome Score (KOOS) [36] for pain, symptoms, function and quality of life.

Preferably, pain in the mammal is reduced as determined by a pain scoring method. The post-operative joint pain is preferably reduced as determined by a pain scoring method. Preferably, pain in the second joint affected with the additional arthritic condition is reduced as determined by a pain scoring method. The post-operative joint pain and the pain in the second joint affected with the additional arthritic condition are preferably reduced as determined by a pain scoring method.

Preferably, pain in a human patient is reduced as determined by using a patient reported outcome measurement instrument. The patient reported outcome measurement instrument is preferably a rating scale. Preferably, the rating scale is the numerical rating scale (NRS) described herein.

Function in the mammal is preferably improved as determined by a function scoring method. Preferably, the joint function of the mammal is improved as determined by a function scoring method. The knee joint function of the mammal is preferably improved as determined by a function scoring method.

Preferably, the knee joint function in a human patient is improved as determined by using a patient reported outcome measurement instrument. The patient reported outcome measurement instrument is preferably the Lysholm Knee Score described herein.

Preferably, the presence of bone marrow edema lesions is reduced. The presence of bone marrow edema lesions associated with osteoarthritis is preferably reduced. Preferably, the presence of bone marrow edema lesions associated with osteoarthritis in the second joint is reduced. The volume of bone marrow edema lesions is preferably reduced. Preferably, the reduction of bone marrow edema lesions is assessed by magnetic resonance imaging (MRI).

Preferably, the presence of bone marrow edema lesions is resolved. The presence of bone marrow edema lesions associated with osteoarthritis is preferably resolved. Preferably, the presence of bone marrow edema lesions associated with osteoarthritis in the second joint is resolved. The resolution of bone marrow edema lesions is preferably assessed by magnetic resonance imaging (MRI).

The present disclosure relates to a composition comprising a polysulfated polysaccharide or an acceptable salt thereof, and an acceptable excipient for the treatment of post-operative joint pain in a mammal.

The present disclosure relates to a composition comprising a polysulfated polysaccharide or an acceptable salt thereof, and an acceptable excipient for use in the treatment of post-operative joint pain in a mammal.

The present disclosure also contemplates the composition described above for the treatment of post-operative joint pain in a mammal or the composition described above for use in the treatment of post-operative joint pain in a mammal, wherein: preferably, the post-operative joint pain is in at least one articulating joint. The at least one articulating joint is preferably selected from the group consisting of: an ankle, elbow, a finger, hip, knee, shoulder, and wrist. Preferably, the at least one articulating joint is a knee.

Preferably, the post-operative pain results from a joint arthroplasty.

The joint arthroplasty is preferably a total joint arthroplasty. Preferably, the total joint arthroplasty is selected from the group consisting of: a total ankle arthroplasty, a total elbow arthroplasty, a total finger arthroplasty, a total hip arthroplasty, a total knee arthroplasty, a total shoulder arthroplasty, and a total wrist arthroplasty. The total joint arthroplasty is preferably a total knee arthroplasty.

The joint arthroplasty is preferably a partial joint arthroplasty. Preferably, the partial joint arthroplasty is selected from the group consisting of: a partial ankle arthroplasty, a partial elbow arthroplasty, a partial finger arthroplasty, a partial hip arthroplasty, a partial knee arthroplasty, a partial shoulder arthroplasty, and a partial wrist arthroplasty. The partial joint arthroplasty is preferably a partial knee arthroplasty.

Preferably, the post-operative joint pain is selected from the group consisting of: acute pain; chronic pain; general pain and persistent pain. The post-operative joint pain is preferably persistent pain. Preferably, the persistent pain is septic persistent pain. The persistent pain is preferably caused by periprosthetic fracture.

Preferably, the persistent pain is aseptic persistent pain. The aseptic persistent pain is preferably intra-articular aseptic persistent pain. Preferably, the intra-articular aseptic persistent pain is caused by a condition selected from the group comprising: aseptic prosthetic loosening, prosthetic wear, instability, recurrent hemarthrosis, patellar maltracking, tendon rupture and stiffness. The aseptic persistent pain is preferably extra-articular aseptic persistent pain. Preferably, the extra-articular aseptic persistent pain is caused by an extra-articular osteoarthritis or extra-articular avascular necrosis.

Preferably, the mammal is suffering from an additional arthritic condition further to the post-operative joint pain. The additional arthritic condition is preferably selected from rheumatoid arthritis or osteoarthritis. Preferably, the additional arthritic condition is rheumatoid arthritis. The additional arthritic condition is preferably osteoarthritis. Preferably, the osteoarthritis is degenerative osteoarthritis. The additional arthritic condition is preferably in a second joint different from the joint affected by the post-operative pain. Preferably, the second joint is one knee joint and the joint affected by the post-operative pain is another knee joint. The second knee joint is preferably the left knee joint and the joint affected by the post-operative pain is the right knee joint in a human patient.

Preferably, the polysulfated polysaccharide is selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

Preferably, the polysulfated polysaccharide is selected from the group consisting of high molecular weight heparin, low molecular weight heparins, the hepran sulfates, pentosan polysulfate (PPS), chondroitin polysulfate and chitosan polysulfate.

Preferably, the polysulfated polysaccharide is selected from the group consisting of high molecular weight heparin, low molecular weight heparins, pentosan polysulfate (PPS), chondroitin polysulfate and chitosan polysulfate.

Preferably, the pentosan polysulfate (PPS) is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

Preferably, the pentosan polysulfate (PPS) is sodium pentosan polysulfate (NaPPS).

In one preferred embodiment, NaPPS is manufactured to the specifications lodged with the US FDA and European Community EMEA by Bene-PharmaChem GmbH & Co KG, Geretsried, Germany.

Preferably, the treatment is by administering the polysulfated polysaccharide or the acceptable salt thereof to the mammal in an effective amount of about 0.5 to about 2 mg/kg of the mammal per dose. The effective amount is preferably in the range of about 0.5 to about 1 mg/kg; about 1.0 to about 1.5 mg/kg or about 1.5 to about 2.0 mg/kg of the mammal per dose. Preferably, the effective amount is about 0.5 mg/kg, about 1.0 mg/kg or about 2.0 mg/kg of the mammal per dose. The effective amount is preferably about 2 mg/kg of the mammal per dose.

Preferably, the treatment is by administering the polysulfated polysaccharide or the acceptable salt thereof to the mammal in an effective amount, wherein the effective amount is a fixed dose in the range of about 25 mg to about 4000 mg. The fixed dose is preferably about 25 mg, about 50 mg, about 75 mg, about 100 mg, about 125 mg, about 150 mg, about 175 mg, about 200 mg, about 225 mg, about 250 mg, about 275 mg or about 300 mg. Preferably, the fixed dose is about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 2000 mg, about 3000 mg or about 4000 mg.

Preferably, the treatment is: by administering an injection; by topical administration; via suppositories or by oral administration. The treatment is preferably by administering an injection. Preferably, the injection is selected from a subcutaneous (SC) injection, an intramuscular (IM) injection, intravenous (IV) injection, intra-articular (IA) injection or a peri-articular injection. The treatment is preferably by administering a subcutaneous (SC) injection. Preferably, the subcutaneous (SC) injection is a slow SC injection.

Preferably, administration to a human is by dosing in a treatment regimen once daily, twice weekly or thrice weekly. Administration to a human is preferably by dosing in a treatment regimen twice weekly. Preferably, administration to a human is by dosing in a treatment regimen twice weekly with a minimum of three days and a maximum of four days between dosages. Administration to a human is preferably by dosing in a treatment regimen twice weekly for three weeks. Preferably, administration to a human is by dosing in a treatment regimen twice weekly for six weeks.

Preferably, the total dose of polysulfated polysaccharide administered in the treatment regimen is about 200 to about 4000 mg.

Preferably, pain in the mammal is reduced as determined by a pain scoring method. The post-operative joint pain is preferably reduced as determined by a pain scoring method. Preferably, pain in the second joint affected with the additional arthritic condition is reduced as determined by a pain scoring method. The post-operative joint pain and the pain in the second joint affected with the additional arthritic condition are preferably reduced as determined by a pain scoring method.

Preferably, pain in a human patient is reduced as determined by using a patient reported outcome measurement instrument. The patient reported outcome measurement instrument is preferably a rating scale. Preferably, the rating scale is the numerical rating scale (NRS) described herein.

Function in the mammal is preferably improved as determined by a function scoring method. Preferably, the joint function of the mammal is improved as determined by a function scoring method. The knee joint function of the mammal is preferably improved as determined by a function scoring method.

Preferably, the knee joint function in a human patient is improved as determined by using a patient reported outcome measurement instrument. The patient reported outcome measurement instrument is preferably the Lysholm Knee Score described herein.

Preferably, the presence of bone marrow edema lesions is reduced. The presence of bone marrow edema lesions associated with osteoarthritis is preferably reduced. Preferably, the presence of bone marrow edema lesions associated with osteoarthritis in the second joint is reduced. The volume of bone marrow edema lesions is preferably reduced. Preferably, the reduction of bone marrow edema lesions is assessed by magnetic resonance imaging (MRI).

Preferably, the presence of bone marrow edema lesions is resolved. The presence of bone marrow edema lesions associated with osteoarthritis is preferably resolved. Preferably, the presence of bone marrow edema lesions associated with osteoarthritis in the second joint is resolved. The resolution of bone marrow edema lesions is preferably assessed by magnetic resonance imaging (MRI).

The present disclosure relates to use of a polysulfated polysaccharide or an acceptable salt thereof, in the treatment of post-operative joint pain in a mammal.

The present disclosure relates to use of a polysulfated polysaccharide or an acceptable salt thereof, in the manufacture of a medicament for the treatment of post-operative joint pain in a mammal.

The present disclosure also contemplates the use of a polysulfated polysaccharide or an acceptable salt thereof, in the treatment of post-operative joint pain in a mammal or the use of a polysulfated polysaccharide or an acceptable salt thereof, in the manufacture of a medicament for the treatment of post-operative joint pain in a mammal, wherein: preferably, the post-operative joint pain is in at least one articulating joint. The at least one articulating joint is preferably selected from the group consisting of: an ankle, elbow, a finger, hip, knee, shoulder, and wrist. Preferably, the at least one articulating joint is a knee.

Preferably, the post-operative pain results from a joint arthroplasty.

The joint arthroplasty is preferably a total joint arthroplasty. Preferably, the total joint arthroplasty is selected from the group consisting of: a total ankle arthroplasty, a total elbow arthroplasty, a total finger arthroplasty, a total hip arthroplasty, a total knee arthroplasty, a total shoulder arthroplasty, and a total wrist arthroplasty. The total joint arthroplasty is preferably a total knee arthroplasty.

The joint arthroplasty is preferably a partial joint arthroplasty. Preferably, the partial joint arthroplasty is selected from the group consisting of: a partial ankle arthroplasty, a partial elbow arthroplasty, a partial finger arthroplasty, a partial hip arthroplasty, a partial knee arthroplasty, a partial shoulder arthroplasty, and a partial wrist arthroplasty. The partial joint arthroplasty is preferably a partial knee arthroplasty.

Preferably, the post-operative joint pain is selected from the group consisting of: acute pain; chronic pain; general pain and persistent pain. The post-operative joint pain is preferably persistent pain. Preferably, the persistent pain is septic persistent pain. The persistent pain is preferably caused by periprosthetic fracture.

Preferably, the persistent pain is aseptic persistent pain. The aseptic persistent pain is preferably intra-articular aseptic persistent pain. Preferably, the intra-articular aseptic persistent pain is caused by a condition selected from the group comprising: aseptic prosthetic loosening, prosthetic wear, instability, recurrent hemarthrosis, patellar maltracking, tendon rupture and stiffness. The aseptic persistent pain is preferably extra-articular aseptic persistent pain. Preferably, the extra-articular aseptic persistent pain is caused by an extra-articular osteoarthritis or extra-articular avascular necrosis.

Preferably, the mammal is suffering from an additional arthritic condition further to the post-operative joint pain. The additional arthritic condition is preferably selected from rheumatoid arthritis or osteoarthritis. Preferably, the additional arthritic condition is rheumatoid arthritis. The additional arthritic condition is preferably osteoarthritis.

Preferably, the osteoarthritis is degenerative osteoarthritis. The additional arthritic condition is preferably in a second joint different from the joint affected by the post-operative pain. Preferably, the second joint is one knee joint and the joint affected by the post-operative pain is another knee joint. The second knee joint is preferably the left knee joint and the joint affected by the post-operative pain is the right knee joint in a human patient.

Preferably, the polysulfated polysaccharide is selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

Preferably, the polysulfated polysaccharide is selected from the group consisting of high molecular weight heparin, low molecular weight heparins, the hepran sulfates, pentosan polysulfate (PPS), chondroitin polysulfate and chitosan polysulfate.

Preferably, the polysulfated polysaccharide is selected from the group consisting of high molecular weight heparin, low molecular weight heparins, pentosan polysulfate (PPS), chondroitin polysulfate and chitosan polysulfate.

Preferably, the pentosan polysulfate (PPS) is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

Preferably, the pentosan polysulfate (PPS) is sodium pentosan polysulfate (NaPPS).

In one preferred embodiment, NaPPS is manufactured to the specifications lodged with the US FDA and European Community EMEA by Bene-PharmaChem GmbH & Co KG, Geretsried, Germany.

Preferably, the treatment is by administering the polysulfated polysaccharide or the acceptable salt thereof to the mammal in an effective amount of about 0.5 to about 2 mg/kg of the mammal per dose. The effective amount is preferably in the range of about 0.5 to about 1 mg/kg; about 1.0 to about 1.5 mg/kg or about 1.5 to about 2.0 mg/kg of the mammal per dose. Preferably, the effective amount is about 0.5 mg/kg, about 1.0 mg/kg or about 2.0 mg/kg of the mammal per dose. The effective amount is preferably about 2 mg/kg of the mammal per dose.

Preferably, the treatment is by administering the polysulfated polysaccharide or the acceptable salt thereof to the mammal in an effective amount, wherein the effective amount is a fixed dose in the range of about 25 mg to about 4000 mg. The fixed dose is preferably about 25 mg, about 50 mg, about 75 mg, about 100 mg, about 125 mg, about 150 mg, about 175 mg, about 200 mg, about 225 mg, about 250 mg, about 275 mg or about 300 mg. Preferably, the fixed dose is about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 2000 mg, about 3000 mg or about 4000 mg.

Preferably, the treatment is: by administering an injection; by topical administration; via suppositories or by oral administration. The treatment is preferably by administering an injection. Preferably, the injection is selected from a subcutaneous (SC) injection, an intramuscular (IM) injection, intravenous (IV) injection, intra-articular (IA) injection or a peri-articular injection. The treatment is preferably by administering a subcutaneous (SC) injection. Preferably, the subcutaneous (SC) injection is a slow SC injection.

Preferably, administration to a human is by dosing in a treatment regimen once daily, twice weekly or thrice weekly. Administration to a human is preferably by dosing in a treatment regimen twice weekly. Preferably, administration to a human is by dosing in a treatment regimen twice weekly with a minimum of three days and a maximum of four days between dosages. Administration to a human is preferably by dosing in a treatment regimen twice weekly for three weeks. Preferably, administration to a human is by dosing in a treatment regimen twice weekly for six weeks.

Preferably, the total dose of polysulfated polysaccharide administered in the treatment regimen is about 200 to about 4000 mg.

Preferably, pain in the mammal is reduced as determined by a pain scoring method. The post-operative joint pain is preferably reduced as determined by a pain scoring method. Preferably, pain in the second joint affected with the additional arthritic condition is reduced as determined by a pain scoring method. The post-operative joint pain and the pain in the second joint affected with the additional arthritic condition are preferably reduced as determined by a pain scoring method.

Preferably, pain in a human patient is reduced as determined by using a patient reported outcome measurement instrument. The patient reported outcome measurement instrument is preferably a rating scale. Preferably, the rating scale is the numerical rating scale (NRS) described herein.

Function in the mammal is preferably improved as determined by a function scoring method. Preferably, the joint function of the mammal is improved as determined by a function scoring method. The knee joint function of the mammal is preferably improved as determined by a function scoring method.

Preferably, the knee joint function in a human patient is improved as determined by using a patient reported outcome measurement instrument. The patient reported outcome measurement instrument is preferably the Lysholm Knee Score described herein.

Preferably, the presence of bone marrow edema lesions is reduced. The presence of bone marrow edema lesions associated with osteoarthritis is preferably reduced. Preferably, the presence of bone marrow edema lesions associated with osteoarthritis in the second joint is reduced. The volume of bone marrow edema lesions is preferably reduced. Preferably, the reduction of bone marrow edema lesions is assessed by magnetic resonance imaging (MRI).

Preferably, the presence of bone marrow edema lesions is resolved. The presence of bone marrow edema lesions associated with osteoarthritis is preferably resolved. Preferably, the presence of bone marrow edema lesions associated with osteoarthritis in the second joint is resolved. The resolution of bone marrow edema lesions is preferably assessed by magnetic resonance imaging (MRI).

EXAMPLE EMBODIMENTS

1. A method for the treatment of post-operative joint pain in a mammal, the method comprising the step of administering a polysulfated polysaccharide or an acceptable salt thereof, to the mammal.

2. The method according to example embodiment 1, wherein the post-operative joint pain is in at least one articulating joint.

3. The method according to example embodiment 2, wherein the at least one articulating joint is selected from the group consisting of: an ankle, elbow, a finger, hip, knee, shoulder, and wrist.

4. The method according to example embodiment 3, wherein the at least one articulating joint is a knee.

5. The method according to any one of example embodiments 1 to 4, wherein the post-operative pain results from a joint arthroplasty.

6. The method according to example embodiment 5, wherein the joint arthroplasty is a total joint arthroplasty.

7. The method according to example embodiment 6, wherein the total joint arthroplasty is selected from the group consisting of: a total ankle arthroplasty, a total elbow arthroplasty, a total finger arthroplasty, a total hip arthroplasty, a total knee arthroplasty, a total shoulder arthroplasty, and a total wrist arthroplasty.

8. The method according to example embodiment 7, wherein the total joint arthroplasty is a total knee arthroplasty.

9. The method according to example embodiment 5, wherein the joint arthroplasty is a partial joint arthroplasty.

10. The method according to example embodiment 9, wherein the partial joint arthroplasty is selected from the group consisting of: a partial ankle arthroplasty, a partial elbow arthroplasty, a partial finger arthroplasty, a partial hip arthroplasty, a partial knee arthroplasty, a partial shoulder arthroplasty, and a partial wrist arthroplasty.

11. The method according to example embodiment 10, wherein the partial joint arthroplasty is a partial knee arthroplasty.

12. The method according to any one of example embodiments 1 to 11, wherein the post-operative joint pain is selected from the group consisting of: acute pain; chronic pain; general pain and persistent pain.

13. The method according to example embodiment 12, wherein the post-operative joint pain is persistent pain.

14. The method according to example embodiment 13, wherein the persistent pain is septic persistent pain.

15. The method according to example embodiment 13, wherein the persistent pain is caused by periprosthetic fracture.

16. The method according to example embodiment 13, wherein the persistent pain is aseptic persistent pain.

17. The method according to example embodiment 16, wherein the aseptic persistent pain is intra-articular aseptic persistent pain.

18. The method according to example embodiment 17, wherein the intra-articular aseptic persistent pain is caused by a condition selected from the group comprising: aseptic prosthetic loosening, prosthetic wear, instability, recurrent hemarthrosis, patellar maltracking, tendon rupture and stiffness.

19. The method according to example embodiment 16, wherein the aseptic persistent pain is extra-articular aseptic persistent pain.

20. The method according to example embodiment 19, wherein the extra-articular aseptic persistent pain is caused by an extra-articular osteoarthritis or extra-articular avascular necrosis.

21. The method according to any one of the preceding example embodiments, wherein the mammal is suffering from an additional arthritic condition further to the post-operative joint pain.

22. The method according to example embodiment 21, wherein the additional arthritic condition is selected from rheumatoid arthritis or osteoarthritis.

23. The method according to example embodiment 22, wherein the additional arthritic condition is rheumatoid arthritis.

24. The method according to example embodiment 22, wherein additional arthritic condition is osteoarthritis.

25. The method according to example embodiment 24, wherein the osteoarthritis is degenerative osteoarthritis.

26. The method according to any one of example embodiments 21 to 25, wherein the additional arthritic condition is in a second joint different from the joint affected by the post-operative pain.

27. The method according to example embodiment 26, wherein the second joint is one knee joint and the joint affected by the post-operative pain is another knee joint.

28. The method according to example embodiment 27, wherein the second knee joint is the left knee joint and the joint affected by the post-operative pain is the right knee joint in a human patient.

29. The method according to any one of example embodiments 1 to 28, wherein the polysulfated polysaccharide is selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

30. The method according to example embodiment 29, wherein the polysulfated polysaccharide is selected from the group consisting of high molecular weight heparin, low molecular weight heparins, the heparan sulfates, pentosan polysulfate (PPS), chondroitin polysulfate and chitosan polysulfate.

31. The method according to example embodiment 30, wherein the pentosan polysulfate (PPS) is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

32. The method according to example embodiment 31, wherein the pentosan polysulfate (PPS) is sodium pentosan polysulfate (NaPPS).

33. The method according to any one of example embodiments 1 to 32, wherein treatment is by administering the polysulfated polysaccharide or the acceptable salt thereof to the mammal in an effective amount of about 0.5 to about 2 mg/kg of the mammal per dose.

34. The method according to example embodiment 33, wherein the effective amount is in the range of about 0.5 to about 1 mg/kg; about 1.0 to about 1.5 mg/kg or about 1.5 to about 2.0 mg/kg of the mammal per dose.

35. The method according to example embodiment 33, wherein the effective amount is about 0.5 mg/kg, about 1.0 mg/kg or about 2.0 mg/kg of the mammal per dose.

36. The method according to example embodiment 33, wherein the effective amount is about 2 mg/kg of the mammal per dose.

37. The method according to any one of example embodiments 1 to 32, wherein the treatment is by administering the polysulfated polysaccharide or the acceptable salt thereof to the mammal in an effective amount, wherein the effective amount is a fixed dose in the range of about 25 mg to about 4000 mg.

38. The method according to example embodiment 37, wherein the fixed dose is about 25 mg, about 50 mg, about 75 mg, about 100 mg, about 125 mg, about 150 mg, about 175 mg, about 200 mg, about 225 mg, about 250 mg, about 275 mg or about 300 mg.

39. The method according to example embodiment 37, wherein the fixed dose is about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 2000 mg, about 3000 mg or about 4000 mg.

40. The method according to any one of example embodiments 1 to 39, wherein the treatment is: by administering an injection; by topical administration; via suppositories or by oral administration.

41. The method according to example embodiment 40, wherein the treatment is by administering an injection.

42. The method according to example embodiment 41, wherein the injection is selected from a subcutaneous (SC) injection, an intramuscular (IM) injection, intravenous (IV) injection, intra-articular (IA) injection or a peri-articular injection.

43. The method according to example embodiment 42, wherein the treatment is by administering a subcutaneous (SC) injection or by administering a slow subcutaneous (SC) injection.

44. The method according to any one of example embodiments 40 to 43, wherein administration to a human is by dosing in a treatment regimen once daily, twice weekly or thrice weekly.

45. The method according to example embodiment 44, wherein administration to a human is by dosing in a treatment regimen twice weekly.

46. The method according to example embodiment 45, wherein administration to a human is by dosing in a treatment regimen twice weekly with a minimum of three days and a maximum of four days between dosages.

47. The method according to example embodiment 46, wherein administration to a human is by dosing in a treatment regimen twice weekly for three weeks or by dosing in a treatment regimen twice weekly for six weeks.

48. The method according to example embodiment 47, wherein the total dose of polysulfated polysaccharide administered in the treatment regimen is about 200 to about 4000 mg.

49. The method according to any of example embodiments 1 to 48, wherein pain in the mammal is reduced as determined by a pain scoring method.

50. The method according to example embodiment 49, wherein the post-operative joint pain is reduced as determined by a pain scoring method.

51. The method according to example embodiment 49, wherein pain in the second joint affected with the additional arthritic condition is reduced as determined by a pain scoring method.

52. The method according to example embodiment 49, wherein the post-operative joint pain and the pain in the second joint affected with the additional arthritic condition are reduced as determined by a pain scoring method.

53. The method according to any one of example embodiments 49 to 52, wherein pain in a human patient is reduced as determined by using a patient reported outcome measurement instrument.

54. The method according to example embodiment 53, wherein the patient reported outcome measurement instrument is a rating scale.

55. The method according to example embodiment 54, wherein the rating scale is the numerical rating scale (NRS) described herein.

56. The method according to any one of example embodiments 1 to 55, wherein function in the mammal is improved as determined by a function scoring method.

57. The method according to example embodiment 56, wherein the joint function of the mammal is improved as determined by a function scoring method.

58. The method according to example embodiment 57, wherein the knee joint function of the mammal is improved as determined by a function scoring method.

59. The method according to example embodiment 58, wherein the knee joint function in a human patient is improved as determined by using a patient reported outcome measurement instrument.

60. The method according to example embodiment 59, wherein the patient reported outcome measurement instrument is the Lysholm Knee Score described herein.

61. The method according to any one of example embodiments 1 to 60, wherein the presence of bone marrow edema lesions is reduced.

62. The method according to example embodiment 61, wherein the presence of bone marrow edema lesions associated with osteoarthritis is reduced.

63. The method according to example embodiment 62, wherein the presence of bone marrow edema lesions associated with osteoarthritis in the second joint is reduced.

64. The method according to any one of example embodiments 61 to 63, wherein the volume of bone marrow edema lesions is reduced.

65. The method according to example embodiment 64, wherein the reduction of bone marrow edema lesions is assessed by magnetic resonance imaging (MRI).

66. The method according to any one of example embodiments 1 to 60, wherein the presence of bone marrow edema lesions is resolved.

67. The method according to example embodiment 66, wherein the presence of bone marrow edema lesions associated with osteoarthritis is resolved.

68. The method according to example embodiment 67, wherein the presence of bone marrow edema lesions associated with osteoarthritis in the second joint is resolved.

69. The method according to any one of example embodiments 66 to 68, wherein the resolution of bone marrow edema lesions is assessed by magnetic resonance imaging (MRI).

70. A composition comprising a polysulfated polysaccharide or an acceptable salt thereof, and an acceptable excipient for the treatment of post-operative joint pain in a mammal.

71. A composition comprising a polysulfated polysaccharide or an acceptable salt thereof, and an acceptable excipient for use in the treatment of post-operative joint pain in a mammal.

72. Use of a polysulfated polysaccharide or an acceptable salt thereof, in the treatment of post-operative joint pain in a mammal.

73. Use of a polysulfated polysaccharide or an acceptable salt thereof, in the manufacture of a medicament for the treatment of post-operative joint pain in a mammal.

74. The composition according to example embodiment 70 or example embodiment 71 or the use according to example embodiment 72 or example embodiment 73, wherein the post-operative joint pain is in at least one articulating joint.

75. The composition or use according to example embodiment 74, wherein the at least one articulating joint is selected from the group consisting of: an ankle, elbow, a finger, hip, knee, shoulder, and wrist.

76. The composition or use according to example embodiment 75, wherein the at least one articulating joint is a knee.

77. The composition or use according to any one of example embodiments 70 to 76, wherein the post-operative pain results from a joint arthroplasty.

78. The composition or use according to example embodiment 77, wherein the joint arthroplasty is a total joint arthroplasty.

79. The composition or use according to example embodiment 78, wherein the total joint arthroplasty is selected from the group consisting of: a total ankle arthroplasty, a total elbow arthroplasty, a total finger arthroplasty, a total hip arthroplasty, a total knee arthroplasty, a total shoulder arthroplasty, and a total wrist arthroplasty.

80. The composition or use according to example embodiment 79, wherein the total joint arthroplasty is a total knee arthroplasty.

81. The composition or use according to example embodiment 77, wherein the joint arthroplasty is a partial joint arthroplasty.

82. The composition or use according to example embodiment 81, wherein the partial joint arthroplasty is selected from the group consisting of: a partial ankle arthroplasty, a partial elbow arthroplasty, a partial finger arthroplasty, a partial hip arthroplasty, a partial knee arthroplasty, a partial shoulder arthroplasty, and a partial wrist arthroplasty.

83. The composition or use according to example embodiment 82, wherein the partial joint arthroplasty is a partial knee arthroplasty.

84. The composition or use according to any one of example embodiments 70 to 83, wherein the post-operative joint pain is selected from the group consisting of: acute pain; chronic pain; general pain and persistent pain.

85. The composition or use according to example embodiment 84, wherein the post-operative joint pain is persistent pain.

86. The composition or use according to example embodiment 85, wherein the persistent pain is septic persistent pain.

87. The composition or use according to example embodiment 85, wherein the persistent pain is caused by periprosthetic fracture.

88. The composition or use according to example embodiment 85, wherein the persistent pain is aseptic persistent pain.

89. The composition or use according to example embodiment 88, wherein the aseptic persistent pain is intra-articular aseptic persistent pain.

90. The composition or use according to example embodiment 89, wherein the intra-articular aseptic persistent pain is caused by a condition selected from the group comprising: aseptic prosthetic loosening, prosthetic wear, instability, recurrent hemarthrosis, patellar maltracking, tendon rupture and stiffness.

91. The composition or use according to example embodiment 90, wherein the aseptic persistent pain is extra-articular aseptic persistent pain.

92. The composition or use according to example embodiment 91, wherein the extra-articular aseptic persistent pain is caused by an extra-articular osteoarthritis or extra-articular avascular necrosis.

93. The composition or use according to any one of the preceding example embodiments, wherein the mammal is suffering from an additional arthritic condition further to the post-operative joint pain.

94. The composition or use according to example embodiment 93, wherein the additional arthritic condition is selected from rheumatoid arthritis or osteoarthritis.

95. The composition or use according to example embodiment 94, wherein the additional arthritic condition is rheumatoid arthritis.

96. The composition or use according to example embodiment 94, wherein additional arthritic condition is osteoarthritis.

97. The composition or use according to example embodiment 96, wherein the osteoarthritis is degenerative osteoarthritis.

98. The composition or use according to any one of example embodiments 93 to 97, wherein the additional arthritic condition is in a second joint different from the joint affected by the post-operative pain.

99. The composition or use according to example embodiment 98, wherein the second joint is one knee joint and the joint affected by the post-operative pain is another knee joint.

100. The composition or use according to example embodiment 99, wherein the second knee joint is the left knee joint and the joint affected by the post-operative pain is the right knee joint in a human patient.

101. The composition according to any one of example embodiments 70 to 100 or use according to any one of example embodiments 72 to 100, wherein the polysulfated polysaccharide is selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

102. The composition or use according to example embodiment 101, wherein the polysulfated polysaccharide is selected from the group consisting of high molecular weight heparin, low molecular weight heparins, the heparan sulfates, pentosan polysulfate (PPS), chondroitin polysulfate and chitosan polysulfate.

103. The composition or use according to example embodiment 102, wherein the pentosan polysulfate (PPS) is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

104. The composition or use according to example embodiment 103, wherein the pentosan polysulfate (PPS) is sodium pentosan polysulfate (NaPPS).

105. The composition according to any one of claims 70 to 104 or use according to any one of example embodiments 72 to 104, wherein treatment is by administering the polysulfated polysaccharide or the acceptable salt thereof to the mammal in an effective amount of about 0.5 to about 2 mg/kg of the mammal per dose.

106. The composition or use according to example embodiment 105, wherein the effective amount is in the range of about 0.5 to about 1 mg/kg; about 1.0 to about 1.5 mg/kg or about 1.5 to about 2.0 mg/kg of the mammal per dose.

107. The composition or use according to example embodiment 105, wherein the effective amount is about 0.5 mg/kg, about 1.0 mg/kg or about 2.0 mg/kg of the mammal per dose.

108. The composition or use according to example embodiment 105, wherein the effective amount is about 2 mg/kg of the mammal per dose.

109. The composition according to any one of example embodiments 70 to 104 or use according to any one of example embodiments 72 to 104, wherein the treatment is by administering the polysulfated polysaccharide or the acceptable salt thereof to the mammal in an effective amount, wherein the effective amount is a fixed dose in the range of about 25 mg to about 4000 mg.

110. The composition or use according to example embodiment 109, wherein the fixed dose is about 25 mg, about 50 mg, about 75 mg, about 100 mg, about 125 mg, about 150 mg, about 175 mg, about 200 mg, about 225 mg, about 250 mg, about 275 mg or about 300 mg.

111. The composition or use according to example embodiment 109, wherein the fixed dose is about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 2000 mg, about 3000 mg or about 4000 mg.

112. The composition according to any one of example embodiments 70 to 111 or use according to any one of example embodiments 74 to 111, wherein the treatment is: by administering an injection; by topical administration; via suppositories or by oral administration.

113. The composition or use according to example embodiment 112, wherein the treatment is by administering an injection.

114. The composition or use according to example embodiment 113, wherein the injection is selected from a subcutaneous (SC) injection, an intramuscular (IM) injection, intravenous (IV) injection, intra-articular (IA) injection or a peri-articular injection.

115. The composition or use according to example embodiment 114, wherein the treatment is by administering a subcutaneous (SC) injection or by administering a slow subcutaneous (SC) injection.

116. The composition or use according to any one of example embodiments 112 to 115, wherein administration to a human is by dosing in a treatment regimen once daily, twice weekly or thrice weekly.

117. The composition or use according to example embodiment 116, wherein administration to a human is by dosing in a treatment regimen twice weekly.

118. The composition or use according to example embodiment 117, wherein administration to a human is by dosing in a treatment regimen twice weekly with a minimum of three days and a maximum of four days between dosages.

119. The composition or use according to example embodiment 118, wherein administration to a human is by dosing in a treatment regimen twice weekly for three weeks or by dosing in a treatment regimen twice weekly for six weeks.

120. The composition or use according to example embodiment 119, wherein the total dose of polysulfated polysaccharide administered in the treatment regimen is about 200 to about 4000 mg.

121. The composition according to any one of example embodiments 70 to 120 or use according to any of example embodiments 72 to 120, wherein pain in the mammal is reduced as determined by a pain scoring method.

122. The composition or use according to example embodiment 121, wherein the post-operative joint pain is reduced as determined by a pain scoring method.

123. The composition or use according to example embodiment 121, wherein pain in the second joint affected with the additional arthritic condition is reduced as determined by a pain scoring method.

124. The composition or use according to example embodiment 121, wherein the post-operative joint pain and the pain in the second joint affected with the additional arthritic condition are reduced as determined by a pain scoring method.

125. The composition or use according to any one of example embodiments 121 to 124, wherein pain in a human patient is reduced as determined by using a patient reported outcome measurement instrument.

126. The composition or use according to example embodiment 125, wherein the patient reported outcome measurement instrument is a rating scale.

127. The composition or use according to example embodiment 126, wherein the rating scale is the numerical rating scale (NRS) described herein.

128. The composition according to any one of example embodiments 70 to 127 or use according to any one of example embodiments 72 to 127, wherein function in the mammal is improved as determined by a function scoring method.

129. The composition or use according to example embodiment 128, wherein the joint function of the mammal is improved as determined by a function scoring method.

130. The composition or use according to example embodiment 129, wherein the knee joint function of the mammal is improved as determined by a function scoring method.

131. The composition or use according to example embodiment 130, wherein the knee joint function in a human patient is improved as determined by using a patient reported outcome measurement instrument.

132. The composition or use according to example embodiment 131, wherein the patient reported outcome measurement instrument is the Lysholm Knee Score described herein.

133. The composition according to any one of example embodiments 70 to 132 or use according to any one of example embodiments 72 to 132, wherein the presence of bone marrow edema lesions is reduced.

134. The composition or use according to example embodiment 133, wherein the presence of bone marrow edema lesions associated with osteoarthritis is reduced.

135. The composition or use according to example embodiment 134, wherein the presence of bone marrow edema lesions associated with osteoarthritis in the second joint is reduced.

136. The composition or use according to any one of example embodiments 133 to 135, wherein the volume of bone marrow edema lesions is reduced.

137. The composition or use according to example embodiment 136, wherein the reduction of bone marrow edema lesions is assessed by magnetic resonance imaging (MRI).

138. The composition according to any one of example embodiments 70 to 132 or use according to any one of example embodiments 72 to 132, wherein the presence of bone marrow edema lesions is resolved.

139. The composition or use according to example embodiment 138, wherein the presence of bone marrow edema lesions associated with osteoarthritis is resolved.

140. The composition or use according to example embodiment 139, wherein the presence of bone marrow edema lesions associated with osteoarthritis in the second joint is resolved.

141. The composition or use according to any one of example embodiments 139 to 140, wherein the resolution of bone marrow edema lesions is assessed by magnetic resonance imaging (MRI).

EXAMPLES

Example 1—Effects of PPS on Clinical Outcomes of Pain and Function in Patient Suffering from Left Knee Osteoarthritis and from Persistent Pain Following Total Right Knee Arthroplasty Example 1 is a study of the safety, tolerability and result of a patient treated with PPS suffering from degenerative osteoarthritis in the left knee with bone marrow edema lesions (BMEL), as assessed by magnetic resonance imaging (MRI), and from persistent pain following total right knee arthroplasty.

The patient was treated with PPS under the TGA Special Access Scheme (B). (Approval to use PPS as treatment for the patient was acquired from Department of Health—Therapeutic Goods Administration, Australian Government under the Special Access Scheme (SAS) since the injectable form of PPS was not a registered product in Australia.)

The patient, a female around 60 years of age, had end stage osteoarthrtis (OA) in her right knee. She underwent a total knee replacement (TKR) in the right knee and had aseptic, persistent pain from that joint post replacement. She also had pain in her left knee (degenerative osteoarthritis) and was recommended to have a TKR in that joint.

She was treated with PPS. The treatment regimen consisted of administration of PPS, at a preferred dose of 2 mg/kg of body weight, twice weekly for three weeks by subcutaneous injection (total of six injections).

Her left (natural) joint went from Numerical Rating Scale (NRS) pain score of 8/10 to 0/10, Lysholm knee function score 58/100 (fair) to 99/100 (excellent) and reduction in bone marrow edema lesion size, as assessed by magnetic resonance imaging (MRI). Pre-treatment MRI (at baseline): showed bone marrow edema stage of up to two thirds; moderate bone marrow edema lesion size of less than 20 mm. Post-treatment MRI (after PPS): showed bone marrow edema stage to be negligible; minimal bone marrow edema lesion size of less than 5 mm.

Following this singular systemic treatment for osteoarthritis of the left knee, the aseptic, persistent pain in the right artificial joint also subsided/stopped and went to zero. The improved pain response in the right knee was concurrent and immediate in relation to the improvement in the left knee. It was further observed that the improved pain response in the right knee was not consequent to the improvement in the left knee or was it associated with rehabilitation or compensatory to the improvement in the left knee.

In summary, the patient in the study had the following characteristics:
High NRS pain score
Fair joint function as determined by Lysholm Knee Score
MRI evidence of Bone Marrow Edema Lesions
The protocol featured the following:
Treatment regimen: 2× weekly subcutaneous injections of PPS (preferred dose 2 mg/kg) for 3 weeks (total of 6 injections)
The clinical outcomes including BMEL assessment, and pain and functional outcome scores are displayed in Table 1.

TABLE 1

Clinical outcomes

| Patient, 60 years of age, F | Before PPS/ NRS Pain | After PPS/ NRS Pain | Before PPS/ Lysholm Knee Score | After PPS/ Lysholm Knee Score | Before PPS/ MRI | After PPS/ MRI |
| --- | --- | --- | --- | --- | --- | --- |
| Left Knee (degenerative OA) | 8 | 0 | 58 | 99 | <20 mm | <5 mm |

Table 1 Legend
Numerical Rating Scale (NRS) [34] is an 11-point scale (0-10). A state of no pain is 0 and the worst pain imaginable is 10.

Lysholm Knee Score [35] is a total score of 0-100 is calculated based on the results from the eight functional components of the Lysholm knee score scale: Limp (5 points), Support (5 points), Locking (15 points), Instability (25 points), Pain (25 points), Swelling (10 points), Stair climbing (10 points), and Squatting (5 points). The total score is assigned to rating categories as follows: 95-100 indicates excellent, 84-94 indicates good, 65-83 indicates fair and <65 indicates poor function.

In conclusion, no adverse events were reported with the use of PPS under the TGA SAS(B) in the patient suffering from pain in the left knee associated with degenerative osteoarthritis and aseptic, persistent pain in the right knee following TKR.

Subcutaneous injection of PPS (preferred dose 2 mg/kg) twice weekly for three weeks (total of six injections) resulted in a clearly visible BMEL reduction, as assessed by magnetic resonance imaging, and improved pain and mobility scores in the left knee joint.

Surprisingly, the post-operative aseptic, persistent pain in the right artificial knee joint also subsided/stopped and went to zero. The surprising improved pain response in the right knee was not consequent to the improvement in the left knee or was it associated with rehabilitation or compensatory to the improvement in the left knee.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

REFERENCES

1. Lim H A, Song E K, Seon J K, Park K S, Shin Y J, Yang H Y, Causes of Aseptic Persistent Pain after Total Knee Arthroplasty. Clinics in Orthopedic Surgery. 2017; 9(1): 50-56.
2. Mayerhoefer M E, Krmaer J, Breitenseher M J, Norden C, Vakil-Adli A, Hofmann S et al. Short-term outcome of painful bone marrow oedema of the knee following oral treatment with iloprost or tramadol: results of an exploratory phase II study of 41 patients. Rheumatology. 2007; 46(9):1460-5.
3. Batemen D, Kennedy J. Non-steroidal anti-inflammatory drugs and elderly patients. British Medical Journal. 1995; 310:817-8.
4. Brandt K D. Should nonsteroidal anti-inflammatory drugs be used to treat osteoarthritis? Rheumatic diseases clinics of North America. 1993; 19(1):29-44.
5. O'Mahony D. Prevention of corticosteroid-induced osteoporosis and fractures. Journal of Clinical Pharmacy and Therapeutics. 1999; 24(2):83-5.
6. Miyata N, Kumagai K, Osaki M, Murata M, Tomita M, Hozumi A, et al. Pentosan reduces osteonecrosis of femoral head in SHRSP. Clinical and experimental hypertension (New York, N.Y.: 1993). 2010; 32(8):511-6.
7. Scully M F, Weerasinghe K M, Ellis V, Djazaeri B, Kakkar V V. Anticoagulant and antiheparin activities of a pentosan polysulphate. Thrombosis Research 1983; 31(1):87-97.
8. Krupinski K, Breddin H K, Casu B. Anticoagulant and antithrombotic effects of chemically modified heparins and pentosan polysulfate. Haemostasis 1990; 20(2):81-92.

9. Shanmugam M, Mody K H. Heparinoid-active sulphated polysaccharides from marine algae as potential blood anticoagulant agents. Current Science 2000; 79(12):1672-1683.
10. Vongchan P, Sajomsang W, Kasinrerk W, Subyen D, Kongrawelert P. Anticoagulant activities of the chitosan polysulfate synthesized from marine crab shell by semi-heterogeneous conditions. Science Asia 2003; 29:115-120.
11. Vinazzer H. Prevention of recurrence of cerebrovascular thromboses. A randomized comparative study acetylsalicylic acid and sodium pentosan polysulfate. Fortschr Med 1987; 105(5):79-85.
12. Losonczy H, David M, Nagy I. Effect of pentosan polysulfate on activated partial thromboplastin time, thrombin time, euglobulin clot lysis and tissue-type plasminogen activator and plasminogen activator inhibitor activities in patients with thromboembolic disease. Semin Thromb Hemost 1991; 17(4):394-8.
13. Anderson V R, Perry C M. Pentosan polysulfate: a review of its use in the relief of bladder pain or discomfort in interstitial cystitis. Drugs 2006; 66(6):821-35.
14. Dimitrakov J, Kroenke K, Steers W D, Berde C, Zurakowski D, Freeman M R, Jackson J L. Pharmacologic management of painful bladder syndrome/interstitial cystitis: a systematic review. Arch Intern Med 2007; 167(18): 1922-9.
15. Davis E L, El Khoudary S R, Talbott E O, Davis J, Regan L R. Safety and efficacy of the use of intravesical and oral pentosan polysulfate sodium for interstitial cystitis: a randomized double-blind clinical trial. J Urol 2008; 179 (1):177-85.
16. WO 2008/144836. Sulphated xylans for treatment or prophylaxis of respiratory diseases.
17. WO 2002/41901. Treatment of osteoporosis.
18. WO 2012/103588. Treatment of bone marrow (oedema) with polysulfated polysaccharides.
19. Davies-Tuck M L, Wluka A E, Wang Y, English D R, Giles G G, Cicuttini F. The natural history of bone marrow lesions in community-based adults with no clinical knee osteoarthritis. Annals of the Rheumatic Diseases. 2009; 68(6):904-8.
20. Felson D T, Chaisson C E, Hill C L, Totterman S M, Gale M E, Skinner K M, et al. The association of bone marrow lesions with pain in knee osteoarthritis. Annals of internal medicine. 2001; 134(7):541-9.
21. Zhai G, Blizzard L, Srikanth V, Ding C, Cooley H, Cicuttini F, et al. Correlates of knee pain in older adults: Tasmanian Older Adult Cohort Study. Arthritis and rheumatism. 2006; 55(2):264-71.
22. Roemer F W, Guermazi A, Javaid M K, Lynch J A, Niu J, Zhang Y, et al. Change in MRI-detected subchondral bone marrow lesions is associated with cartilage loss: the MOST Study. A longitudinal multicentre study of knee osteoarthritis. Ann Rheum Dis. 2009; 68(9): 1461-5.
23. Hunter D J, Zhang Y, Niu J, Goggins J, Amin S, LaValley M P, et al. Increase in bone marrow lesions associated with cartilage loss: a longitudinal magnetic resonance imaging study of knee osteoarthritis. Arthritis and rheumatism. 2006; 54(5):1529-35.
24. Wluka A E, Wang Y, Davies-Tuck M, English D R, Giles G G, Cicuttini F M. Bone marrow lesions predict progression of cartilage defects and loss of cartilage volume in healthy middle-aged adults without knee pain over 2 yrs. Rheumatology (Oxford, England). 2008; 47(9):1392-6.
25. Wluka A E, Hanna F, Davies-Tuck M, Wang Y, Bell R J, Davis S R, et al. Bone marrow lesions predict increase in knee cartilage defects and loss of cartilage volume in middle-aged women without knee pain over 2 years. Ann Rheum Dis. 2009; 68(6):850-5.
26. Starr A M, Wessely M A, Albastaki U, Pierre-Jerome C, Kettner N W. Bone marrow edema: pathophysiology, differential diagnosis, and imaging. Acta radiologica (Stockholm, Sweden: 1987). 2008; 49(7):771-86.
27. Altahawi F F, Blount K J, Morley N P, Raithel E, Omar I M. Comparing an accelerated 3D fast spin-echo sequence (CS-SPACE) for knee 3-T magnetic resonance imaging with traditional 3D fast spin-echo (SPACE) and routine 2D sequences. Skeletal radiology. 2017; 46(1):7-15.
28. Felson D T, McLaughlin S, Goggins J, LaValley M P, Gale M E, Totterman S, et al. Bone marrow edema and its relation to progression of knee osteoarthritis. Annals of internal medicine. 2003; 139(5 Pt 1):330-6.
29. Raynauld J P, Martel-Pelletier J, Berthiaume M J, Abram F, Choquette D, Haraoui B, et al. Correlation between bone lesion changes and cartilage volume loss in patients with osteoarthritis of the knee as assessed by quantitative magnetic resonance imaging over a 24-month period. Ann Rheum Dis. 2008; 67(5):683-8.
30. Tanamas S K, Wluka A E, Pelletier J P, Pelletier J M, Abram F, Berry P A, et al. Bone marrow lesions in people with knee osteoarthritis predict progression of disease and joint replacement: a longitudinal study. Rheumatology (Oxford, England). 2010; 49(12):2413-9.
31. Lowitz T, Museyko O, Bousson V, Laouisset L, Kalender W A, Laredo J D, et al. Bone marrow lesions identified by MRI in knee osteoarthritis are associated with locally increased bone mineral density measured by QCT. Osteoarthritis and cartilage. 2013; 21(7):957-64.
32. Laslett L L, Dore D A, Quinn S J, Boon P, Ryan E, Winzenberg T M, et al. Zoledronic acid reduces knee pain and bone marrow lesions over 1 year: a randomised controlled trial. Ann Rheum Dis. 2012; 71(8):1322-8.
33. Varenna M, Zucchi F, Failoni S, Becciolini A, Berruto M. Intravenous neridronate in the treatment of acute painful knee osteoarthritis: a randomized controlled study. Rheumatology (Oxford, England). 2015; 54(10):1826-32.
34. Hjermstad M J, Fayers P M, Haugen D F, Caraceni A, Hanks G W, Loge J H, et al. Studies comparing Numerical Rating Scales, Verbal Rating Scales, and Visual Analogue Scales for assessment of pain intensity in adults: a systematic literature review. Journal of pain and symptom management. 2011; 41(6):1073-93.
35. Briggs K K, Kocher M S, Rodkey W G, Steadman J R. Reliability, validity, and responsiveness of the Lysholm knee score and Tegner activity scale for patients with meniscal injury of the knee. The Journal of bone and joint surgery American volume. 2006; 88(4):698-705.
36. Roos E M, Lohmander L S. Knee injury and Osteoarthritis Outcome Score (KOOS): from joint injury to osteoarthritis. Health Qual Life Outcomes 2003; 1:64.

The invention claimed is:

1. A method for the treatment of aseptic post-operative intra-articular joint pain resulting from a joint arthroplasty performed on a mammal, the method comprising the steps of:
(i) identifying the mammal as suffering from aseptic post-operative intra-articular joint pain which is the direct result of a joint arthroplasty, wherein the mammal is post-operatively not suffering from osteolysis, osteoarthritis or bone marrow edema in said joint; and (ii) administering, within 12 months post-operatively, an amount of pentosan polysulfate or an acceptable salt thereof, to the mammal, effective to alleviate said aseptic post-operative intra-articular joint pain resulting from the joint arthroplasty.

2. The method according to claim 1, wherein the post-operative joint pain is in at least one articulating joint selected from the group consisting of: an ankle, elbow, a finger, hip, knee, shoulder, and wrist.

3. The method according to claim 2, wherein the at least one articulating joint is a knee.

4. The method according to claim 1, wherein the joint arthroplasty is a partial joint arthroplasty selected from the group consisting of: a partial ankle arthroplasty, a partial elbow arthroplasty, a partial finger arthroplasty, a partial hip arthroplasty, a partial knee arthroplasty, a partial shoulder arthroplasty, and a partial wrist arthroplasty.

5. The method according to claim 1, wherein the joint arthroplasty is a total joint arthroplasty selected from the group consisting of: a total ankle arthroplasty, a total elbow arthroplasty, a total finger arthroplasty, a total hip arthroplasty, a total knee arthroplasty, a total shoulder arthroplasty, and a total wrist arthroplasty.

6. The method according to claim 1, wherein the post-operative joint pain is selected from the group consisting of: acute pain; chronic pain; and persistent pain.

7. The method according to claim 6, wherein the persistent pain is intra-articular persistent.

8. The method according to claim 1, wherein the mammal is suffering from an additional arthritic condition further to the post-operative joint pain, in a second joint different from the joint affected by the post-operative pain, wherein the additional arthritic condition is selected from the group consisting of: rheumatic arthritis, osteoarthritis and degenerative osteoarthritis.

9. The method according to claim 8, wherein the second joint is one knee joint and the joint affected by the post-operative pain is another knee joint.

10. The method according to claim 1, wherein the pentosan polysulfate (PPS) is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

11. The method according to claim 1, wherein treatment is by administering the polysulfated polysaccharide or the acceptable salt thereof to the mammal in an effective amount of about 0.5 to about 2 mg/kg; about 0.5 to about 1 mg/kg; about 1.0 to about 1.5 mg/kg or about 1.5 to about 2.0 mg/kg of the mammal per dose or wherein the effective amount is a fixed dose in the range of about 25 mg to about 4000 mg.

12. The method according to claim 11, wherein the fixed dose is about 25 mg, about 50 mg, about 75 mg, about 100 mg, about 125 mg, about 150 mg, about 175 mg, about 200 mg, about 225 mg, about 250 mg, about 275 mg, about 300 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 2000 mg, about 3000 mg or about 4000 mg.

13. The method according to claim 1, wherein the treatment is: by administering a subcutaneous (SC) injection, an intramuscular (IM) injection, intravenous (IV) injection, intra-articular (IA) injection or a peri-articular injection; by topical administration; via suppositories or by oral administration.

14. The method according to claim 13, wherein administration to a human patient is by dosing in a treatment regimen once daily, twice weekly or thrice weekly.

15. The method according to claim 14, wherein administration to a human is by dosing in a treatment regimen twice weekly with a minimum of three days and a maximum of four days between dosages.

16. The method according to claim 1, wherein pain in a human patient is reduced as determined by using the numerical rating scale (NRS).

17. The method according to claim 9, wherein the function of the knee joint with post-operative pain and/or function of the knee joint with the additional arthritic condition in a human patient is improved as determined by using the Lysholm Knee Score.

18. The method according to claim 1, wherein the presence of bone marrow edema lesions is reduced in a second joint different from the joint affected by the post-operative pain.

19. The method according to claim 1, wherein the mammal is treated for the aseptic post-operative intra-articular joint pain within 6 months of the joint arthroplasty.

20. A method for the treatment of aseptic post-operative intra-articular joint pain resulting from a joint arthroplasty performed on a mammal, the method comprising the steps of:
(i) performing a joint arthroplasty on a joint of a mammal in a manner so as to alleviate pain present within the joint;
(ii) identifying the mammal as suffering from aseptic post-operative intra-articular joint pain which is the direct result of the joint arthroplasty, wherein the mammal is post-operatively not suffering from osteolysis, osteoarthritis or bone marrow edema in said joint; and
(iii) treating the aseptic post-operative intra-articular joint pain arising from said joint arthroplasty, within 12 months post-operatively, by injecting an effective amount of sodium pentosan polysulfate into said joint.

21. A method for the treatment of aseptic post-operative intra-articular joint pain resulting from a joint arthroplasty performed on a mammal, the method comprising the steps of:
(i) determining that pain present in a joint of the mammal is susceptible to pain relief, by performing a joint arthroplasty on said joint; and
(ii) identifying the mammal as suffering from aseptic post-operative intra-articular joint pain which is the direct result of the joint arthroplasty, wherein the mammal is post-operatively not suffering from osteolysis, osteoarthritis or bone marrow edema in said joint; and
(iii) treating the aseptic post-operative intra-articular joint pain arising from said joint arthroplasty, within 12 months post-operatively, by injecting an effective amount of sodium pentosan polysulfate into said joint.

22. A method for the treatment of aseptic post-operative intra-articular joint pain resulting from a joint arthroplasty performed on a subject, the method comprising the steps of:
(i) selecting a subject who has had a joint arthroplasty;
(ii) diagnosing the subject as suffering from aseptic post-operative intra-articular joint pain which is a result of said joint arthroplasty, wherein the subject is post-operatively not suffering from osteolysis, osteoarthritis or bone marrow edema in said joint; and
(iii) administering, within 12 months post-operatively, based on said diagnosis of step (ii), an amount of sodium pentosan polysulfate to the subject effective to alleviate said aseptic post-operative intra-articular joint pain resulting from said joint arthroplasty.

23. A method for the treatment of aseptic post-operative intra-articular joint pain resulting from a joint arthroplasty performed on a subject, the method comprising the steps of:
(i) selecting a subject who has had a joint arthroplasty within the preceding 12 months and who has been diagnosed as suffering from aseptic post-operative intra-articular joint pain which is a result of said joint arthroplasty, wherein the subject is post-operatively not suffering from osteolysis, osteoarthritis or bone marrow edema in said joint; and
(ii) administering, within 12 months post-operatively, based on said diagnosis of step (i), an amount of sodium pentosan polysulfate to the subject effective to alleviate said aseptic post-operative intra-articular joint pain resulting from said joint arthroplasty.

* * * * *